(12) United States Patent
Wieters et al.

(10) Patent No.: US 11,672,411 B2
(45) Date of Patent: Jun. 13, 2023

(54) DEFLECTION PRISM ASSEMBLY FOR AN ENDOSCOPE HAVING A LATERAL VIEWING DIRECTION, ENDOSCOPE, AND METHOD FOR ASSEMBLING A DEFLECTION PRISM ASSEMBLY

(71) Applicant: OLYMPUS WINTER & IBE GMBH, Hamburg (DE)

(72) Inventors: Martin Wieters, Barsbuettel (DE); Alrun Thuemen, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 514 days.

(21) Appl. No.: 16/852,962

(22) Filed: Apr. 20, 2020

(65) Prior Publication Data

US 2020/0237195 A1    Jul. 30, 2020

Related U.S. Application Data

(63) Continuation of application No. PCT/EP2018/077182, filed on Oct. 5, 2018.

(30) Foreign Application Priority Data

Oct. 20, 2017   (DE) .................... 10 2017 124 593.6

(51) Int. Cl.
*A61B 1/00*     (2006.01)
*G02B 5/04*    (2006.01)
(Continued)

(52) U.S. Cl.
CPC ...... *A61B 1/00177* (2013.01); *A61B 1/00096* (2013.01); *A61B 1/00179* (2013.01);
(Continued)

(58) Field of Classification Search
CPC ............ A61B 1/00096; A61B 1/00177; A61B 1/00179; A61B 1/00181; A61B 1/00183; A61B 1/00193; G02B 7/18; G02B 7/1805
See application file for complete search history.

(56) References Cited

U.S. PATENT DOCUMENTS 5,573,493 A    11/1996   Sauer et al.
5,866,048 A *  2/1999   Van Domelen ...... G02B 7/1805
                                                             359/407
(Continued)

FOREIGN PATENT DOCUMENTS

CN    204009189 U    12/2014
CN    106030350 A    10/2016
(Continued)

OTHER PUBLICATIONS

International Search Report dated Dec. 21, 2018 received in PCT/EP2018/077182.

*Primary Examiner* — Aaron B Fairchild
*Assistant Examiner* — Stephen Floyd London
(74) *Attorney, Agent, or Firm* — Scully, Scott, Murphy & Presser, P.C.

(57) ABSTRACT

A deflection prism assembly for an endoscope having a lateral viewing direction, the deflection prism assembly including: a prism holder; and a deflection prism accommodated in the prism holder; wherein the deflection prism has a light outlet surface and an opposite light inlet surface arranged obliquely to the light outlet surface, the deflection prism further having a lateral surface extending between the light inlet surface and the light outlet surface; and the prism holder accommodates the deflection prism such that the prism holder surrounds less than all regions of the lateral surface of the deflection prism.

16 Claims, 5 Drawing Sheets

(51) Int. Cl.
  *G02B 17/04*    (2006.01)
  *G02B 23/24*    (2006.01)
  *G02B 7/18*     (2021.01)
  *A61B 1/04*     (2006.01)

(52) U.S. Cl.
  CPC ............. *G02B 5/04* (2013.01); *G02B 7/1805* (2013.01); *G02B 17/045* (2013.01); *G02B 23/243* (2013.01); *G02B 23/2476* (2013.01); *A61B 1/0011* (2013.01); *A61B 1/04* (2013.01)

(56) References Cited

U.S. PATENT DOCUMENTS

| | | | | |
|---|---|---|---|---|
| 5,980,453 | A * | 11/1999 | Forkey | H04N 13/296 600/176 |
| 6,537,209 | B1 * | 3/2003 | Pinkhasik | A61B 1/00101 600/176 |
| 7,280,283 | B1 | 10/2007 | Kasai | |
| 10,085,621 | B2 | 10/2018 | Wieters | |
| 10,310,149 | B1 * | 6/2019 | Dubrall | G02B 27/022 |
| 2002/0022767 | A1 * | 2/2002 | Dohi | G02B 5/06 600/137 |
| 2003/0137726 | A1 * | 7/2003 | Seifert | G02B 7/008 359/407 |
| 2007/0073108 | A1 | 3/2007 | Takahashi | |
| 2008/0088730 | A1 * | 4/2008 | Harada | H04N 5/2253 348/337 |
| 2009/0067067 | A1 * | 3/2009 | Yamaya | A61B 1/00183 359/813 |
| 2011/0199471 | A1 | 8/2011 | Tomioka | |
| 2012/0182458 | A1 * | 7/2012 | Ishii | H04N 5/2254 359/833 |
| 2013/0120647 | A1 * | 5/2013 | Negishi | H04N 5/2254 348/374 |
| 2014/0135577 | A1 * | 5/2014 | Baumann | A61B 1/055 600/109 |
| 2014/0152972 | A1 * | 6/2014 | Robertson | G02B 7/08 359/872 |
| 2014/0320962 | A1 | 10/2014 | Ando et al. | |
| 2015/0238068 | A1 | 8/2015 | Rose | |
| 2015/0277078 | A1 * | 10/2015 | Wiley | B32B 37/142 359/811 |
| 2016/0026067 | A1 * | 1/2016 | Feinbloom | G02B 7/1805 396/544 |
| 2016/0238849 | A1 * | 8/2016 | Sugihara | G02B 7/1805 |
| 2016/0291312 | A1 * | 10/2016 | Satake | A61B 1/05 |
| 2016/0345804 | A1 | 12/2016 | Wieters et al. | |
| 2016/0345805 | A1 | 12/2016 | Wieters et al. | |
| 2017/0082848 | A1 * | 3/2017 | Kudo | A61B 1/00101 |
| 2018/0024348 | A1 | 1/2018 | Wieters et al. | |

FOREIGN PATENT DOCUMENTS

| | | |
|---|---|---|
| DE | 24 58 306 A1 | 6/1975 |
| DE | 10 2011 078 968 A1 | 1/2013 |
| DE | 10 2012 220 578 A1 | 5/2014 |
| DE | 10 2014 202 669 A1 | 8/2015 |
| DE | 10 2014 211 367 A1 | 12/2015 |
| DE | 10 2014 113 352 A1 | 3/2016 |
| DE | 10 2015 101 624 A1 | 8/2016 |
| DE | 10 2014 202 612 B4 | 8/2017 |
| DE | 10 2011 090 132 B4 | 9/2017 |
| EP | 2 730 210 A1 | 5/2014 |
| JP | 2000-221416 A | 8/2000 |
| JP | 2014-119474 A | 6/2014 |
| JP | 2015-507497 A1 | 3/2015 |
| JP | 2016-212194 A | 12/2016 |
| WO | 2016/041637 A1 | 3/2016 |

* cited by examiner

DEFLECTION PRISM ASSEMBLY FOR AN ENDOSCOPE HAVING A LATERAL VIEWING DIRECTION, ENDOSCOPE, AND METHOD FOR ASSEMBLING A DEFLECTION PRISM ASSEMBLY

CROSS-REFERENCE TO RELATED APPLICATION

The present application is a continuation of PCT/EP2018/077182 filed on Oct. 5, 2018, which is based upon and claims the benefit to DE 10 2017 124 593.6 filed on Oct. 20, 2017, the entire contents of each of which are incorporated herein by reference.

BACKGROUND

Field

The present disclosure relates to a deflection prism assembly for an endoscope having a lateral viewing direction, an endoscope and a method for assembling a deflection prism assembly.

Prior Art

In endoscopy, it is frequently meaningful to deploy endoscopes having viewing directions which deviate from 0°, that is to say from looking forward. In this case, these endoscopes are referred to as endoscopes having a lateral viewing direction.

Such an endoscope having a lateral viewing direction is disclosed, for example, in DE 10 2011 090 132 A1.

Distal deflection prisms which are constructed from multiple sub-prisms, are commonly deployed in endoscopes, in particular video endoscopes, of this type. The object of a deflection prism consists of deflecting the obliquely incident light so that, after exiting from the deflection prism, it runs parallel to the endoscope axis.

In order to fix the deflection prism in the endoscope, the latter is accommodated in a prism holder. Said prism holder is commonly cylindrical and encloses the deflection prism completely. The deflection prism and the prism holder form a deflection prism assembly.

In order to achieve improved optical properties and a larger field of view, a larger deflection prism can be deployed, since this increases the region from which light can enter the endoscope.

However, it is very important, especially in the case of medical endoscopes, that the outside diameter of the endoscope shaft is as small as possible, thus making possible minimally invasive endoscopic examinations of patients.

However, a small outside diameter of the endoscope shaft requires that the deflection prism assembly is also as small as possible. Consequently, the requirements of the endoscope, according to which the latter is to have a high image quality and a large light intensity, on the one hand, and as small an outside diameter as possible, on the other hand, conflict with one another.

SUMMARY

Hence, an object is to provide a deflection prism assembly, an endoscope and a method for assembling a deflection prism assembly, with which an improvement of the optical properties is achieved, without enlarging the outside diameter of the endoscope shaft.

Such object can be solved by a deflection prism assembly for an endoscope having a lateral viewing direction, comprising a prism holder and a deflection prism which is accommodated in the prism holder, wherein the deflection prism has a light outlet surface and an opposite light inlet surface arranged obliquely thereto, and a lateral surface extends between the inlet and outlet surfaces, wherein the prism holder accommodates the deflection prism in such a way that the prism holder surrounds certain regions of the lateral surface of the deflection prism.

The light inlet surface is aligned so that the angle between the light inlet surface and the light outlet surface corresponds to the oblique viewing direction of the endoscope. The lateral surface extends between the light inlet surface and the light outlet surface. All the regions of the surface of the deflection prism, which do not belong to the light inlet surface or light outlet surface, are consequently part of the lateral surface. In the context of the present description, the term "enclosing certain regions" is understood to mean that, compared with a cylindrical prism holder, regions of the prism holder are omitted.

The deflection prism is advantageously enlarged in regions which are not surrounded by the prism holder. The deflection prism is enlarged by exactly the volume which has been omitted by the enclosing of only certain regions of the deflection prism. This enlargement of the deflection prism does not lead to an increase in the circumference of the deflection prism assembly and it does not, therefore, lead to an increase in the diameter of the endoscope shaft. At the same time, due to the enlargement of the deflection prism, more light enters the endoscope so that the optical properties of the endoscope improve and the light intensity of the endoscope increases.

The prism holder can only enclose the lateral surface in the regions which are necessary for a secure fixing and an exact alignment of the deflection prism in the prism holder.

The prism holder can be formed in such a way that the latter does not completely enclose the deflection prism at any of the possible outer circumferences of the deflection prism, wherein the outer circumferences run parallel to the light outlet surface on the lateral surface of the deflection prism.

In order to align the deflection prism in the prism holder exactly, it is not necessary for the prism holder to enclose the lateral surface along a complete outer circumference. For example, regions of the prism holder, which extend along the lateral surface from the light inlet surface to the light outlet surface, can consequently be completely omitted. This can produce a space-saving design of the prism holder. By enlarging the deflection prism in the regions which are not enclosed by the prism holder, the optical properties of the endoscope are improved.

The prism holder can comprise a first part and a second part, wherein the first part extends along an entire length of the deflection prism and the second part extends along a section of the length of the deflection prism, wherein the length is an extension of the deflection prism in the direction of a perpendicular to the light outlet plane.

The first part of the prism holder consequently extends along the entire length of the lateral surface between the light outlet surface and the light inlet surface. As a result, the first part of the prism holder is suitable for fixing the deflection prism to the prism holder. The first part may only enclose the lateral surface of the deflection prism in the angle range of the outer circumference which is necessary for a secure fixing. For example, the first part of the prism holder may only enclose the lateral surface for approximately 150° along the outer circumference.

The second part only extends along a section of the length of the lateral surface, wherein this section extends from the light outlet surface in the direction of the light inlet surface. The lateral surface is consequently not surrounded by the prism holder between the light inlet surface and the second part of the prism holder. In this region, the deflection prism can be enlarged in order to further improve the optical properties of the endoscope.

Due to the oblique arrangement, the light inlet surface can have a near partial surface and a distant partial surface with respect to the light outlet surface, wherein the first part of the prism holder extends from the light outlet surface to the near partial surface and the second part of the prism holder extends from the light outlet surface in the direction of the distant partial surface.

The consequence of the oblique arrangement of the light inlet surface is that the reflections of the incident light in the deflection prism substantially take place in the upper part of the deflection prism. The upper part of the deflection prism is the part of the deflection prism, which extends from the distant partial surface to the reflection surface, wherein the reflection surface is the part of the lateral surface which reflects incident light a first time. By contrast, the lower part of the deflection prism extends from the near partial surface to the light outlet surface.

The first part of the prism holder consequently surrounds certain regions of the lateral surface in the lower part of the deflection prism, whilst the second part of the prism holder surrounds certain regions of the lateral surface in the upper part of the deflection prism.

Since the beam path of the incident light substantially runs in the upper part of the deflection prism, the lower part can be used for fixing. The first part of the prism holder, which surrounds this lower part of the deflection prism, therefore extends along the entire length of the lateral surface so that a secure fixing of the deflection prism to the lateral surface is made possible.

In order to achieve a large light intensity of the endoscope, the prism holder is omitted in certain regions in the upper part of the deflection prism and the deflection prism is enlarged in this region. For this reason, the second part of the prism holder only extends along a section of the length of the lateral surface.

The second part of the prism holder can comprise an upper holding surface, wherein a reflection surface of the deflection prism is fixed to the upper holding surface.

Since the incident light is reflected by the reflection surface, the region behind the reflection surface is not optically required. The second part of the prism holder is arranged in this region.

Due to such an arrangement of the second part of the prism holder, the latter can be used to fix the deflection prism, without this negatively influencing the optical properties of the endoscope. To this end, a surface of the second part is configured as an upper holding surface, to which the reflection surface is fixed, for example, by means of adhesive.

The first part of the prism holder can comprise a lower holding surface and the deflection prism can comprise a bottom surface having a complementary shape, wherein the lower holding surface and the bottom surface are arranged perpendicularly to the light outlet surface and the bottom surface is fixed to the lower holding surface.

Since the lower part of the deflection prism is not optically utilized, this is used to fix the deflection prism to the prism holder. To this end, the deflection prism is designed, for example by grinding off, so that it has a bottom surface which is perpendicular to the outlet surface. The prism holder has a holding surface having a complementary shape, to which the bottom surface is fixed. This fixing is realized, for example, by means of an adhesive.

The deflection prism can be fixed both to the upper holding surface of the second part of the prism holder and to the lower holding surface of the first part of the prism holder. In this way, a secure fixing of the deflection prism in the prism holder is achieved.

The first part of the prism holder can comprise at least two adjacent lower holding surfaces and the deflection prism can comprise bottom surfaces associated with the lower holding surfaces.

If the deflection prism only has a single bottom surface, the fixing of the deflection prism to the prism holder is susceptible with respect to shear forces which act laterally on the deflection prism. This might possibly result in the deflection prism slipping in the prism holder, which would result in a deterioration of the optical properties of the endoscope. In order to counter these shear forces, multiple bottom surfaces and multiple lower holding surfaces can be used. These bottom surfaces (and consequently also the lower holding surfaces having a complementary shape) form an angle. At the same time, all of the bottom surfaces are oriented perpendicularly to the light outlet surface.

A total angle, that is to say the total of the individual angles of the adjacent lower holding surfaces, can be between 60° and 120°, such as approximately 90°.

In order to calculate the total angle, the angle between the adjacent surfaces is determined for all of the adjacent lower holding surfaces, and these angles are added up.

In order to counter the shear forces, two lower holding surfaces which are located at an angle of 90° to one another would be possible. Admittedly, the use of two surfaces means that the first part of the prism holder must be designed to be so large that the first part of the prism holder surrounds the outer circumference of the lateral surface in an angle range of approximately 180°.

This could have negative repercussions on the optical properties of the endoscope and, in addition, makes centering the deflection prism difficult, since as large as possible an outer circumference of the lateral surface, which is not surrounded by the prism holder, is required for this.

A compromise between as large as possible an outer circumference of the lateral surface of the deflection prism and as large as possible a resistance with respect to shear forces must therefore be found. Such a compromise involves, for example, using three lower holding surfaces which are each located at an angle of at least roughly 45° to one another. This makes it possible to obtain a total angle of approximately 90° and, at the same time, to realize an outer circumference of the lateral surface, which is not surrounded by the first part of the prism holder, of approximately 210°.

The first part and the second part can be connected by a stop of the prism holder, wherein the stop can be annular. The stop can comprise a contact surface which is plane parallel to the light outlet surface of the deflection prism, wherein the light outlet surface rests on certain regions of the contact surface.

The stop can be arranged proximally to the deflection prism. Although it has an annular form, it does not enclose the deflection prism as a result.

By bringing the light outlet surface to rest on the contact surface, a tilting of the deflection prism is minimized. The contact surface is, exactly like the light outlet surface, arranged perpendicularly to the endoscope axis. This makes it possible to align the inclination of the deflection prism exactly with respect to the endoscope axis. The contact surface can only rest on the region of the light outlet surface, which is not optically utilized.

An adhesive gap having a gap width can be configured between the lower holding surface and the associated bottom surface and/or between the upper holding surface and the associated reflection surface, wherein the gap width is so large that, taking account of production tolerances, the lower holding surface does not rest on any point of the bottom surface and/or the upper holding surface does not rest on any point of the reflection surface, if the light outlet surface rests on certain regions of the contact surface.

Since the inclination can be aligned by bringing the light outlet surface to rest on the contact surface, the deflection prism does not have to rest on any other point of the prism holder, since this would have a negative effect on the alignment.

Hence, the deflection prism and the prism holder can be produced so that there is in each case a gap between the upper holding surface and the associated reflection surface and between the lower holding surfaces and the associated bottom surfaces, so that the deflection prism and the prism holder only touch in the region of the contact surface. The gaps are in particular utilized as adhesive gaps for fixing.

At least one third, such as at least two thirds, of an outer circumference of the lateral surface can be circular. Furthermore, at least one third of an outer circumference of the prism holder, such as a complete outer circumference of the prism holder, can be circular.

The outer circumference of the lateral surface and of the prism holder can have the same radius.

Due to the circular outer circumference of the lateral surface and of the prism holder, these can be aligned with respect to the endoscope axis during installation in an endoscope. The at least partially circular outer circumference makes it possible for the outer circumference of the deflection prism and of the prism holder to be brought into alignment with one another and to subsequently be aligned with respect to the endoscope axis, i.e. centered. Such an alignment of the deflection prism and of the prism holder prevents vignetting and image cutting and consequently guarantees an improvement of the image quality.

In addition, such object can be solved by an endoscope comprising a deflection prism assembly in accordance with one of the previously indicated embodiments.

Furthermore, the object can be solved by a method for assembling a deflection prism assembly, comprising a prism holder and a deflection prism, for an endoscope having a lateral viewing direction, comprising the following method steps:

centering the deflection prism with respect to the prism holder by bringing an outer circumference of a lateral surface of the deflection prism and an outer circumference of the prism holder into alignment, aligning the deflection prism with respect to the prism holder by bringing certain regions of a light outlet surface of the deflection prism to rest on a contact surface of the prism holder, and fixing at least one bottom surface of the deflection prism to at least one lower holding surface of the prism holder and fixing a reflection surface of the deflection prism to an upper holding surface of the prism holder.

The same or similar advantages apply to the endoscope and the method for assembling a deflection prism assembly as have already been explained with respect to the deflection prism assembly so that repetitions shall be dispensed with.

Further features will become evident from the description of embodiments, together with the claims and the appended drawings. Embodiments can fulfill individual features or a combination of several features.

BRIEF DESCRIPTION OF THE DRAWINGS

The embodiments will be described below without limiting the general concept of the invention by means of exemplary embodiments with reference to the drawings, wherein reference is expressly made to the drawings regarding all of the details which are not explained in greater detail in the text, wherein.

In the drawings, the same or similar elements and/or parts are, in each case, provided with the same reference numerals so that they are not introduced again in each case.

DETAILED DESCRIPTION

Figure 1:
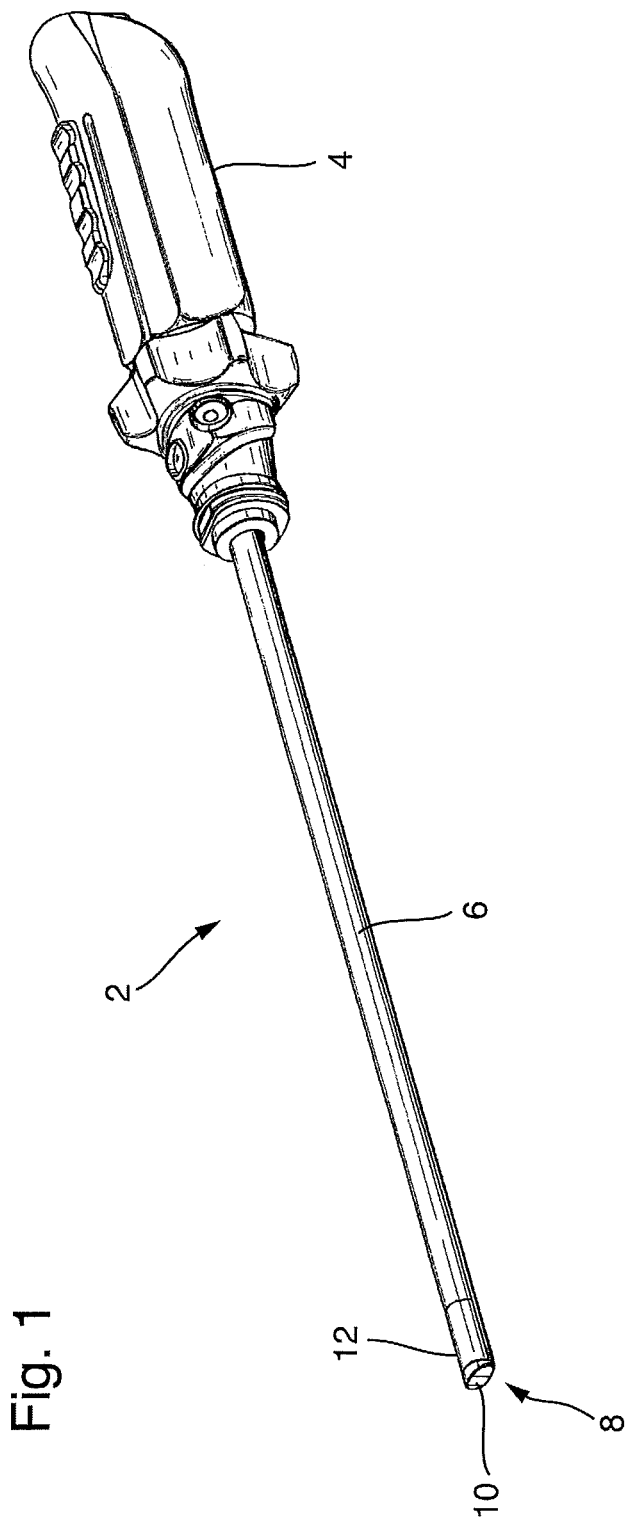
FIG. 1 illustrates a schematically simplified, perspective diagram of an endoscope.

FIG. 1 shows an endoscope 2 having a lateral viewing direction. On a proximal end of the endoscope 2 there is located a handle 4, to which a shaft 6 is joined. On a distal end 8 of the shaft 6 there is located an inlet window 10, by which light beams from an observation or operation field located distally in front of the distal end 8 enter the interior of the shaft 6. In a distal end region 12 of the shaft 6, a deflection prism is arranged as part of a deflection prism assembly within the shaft 6.

Figure 2:
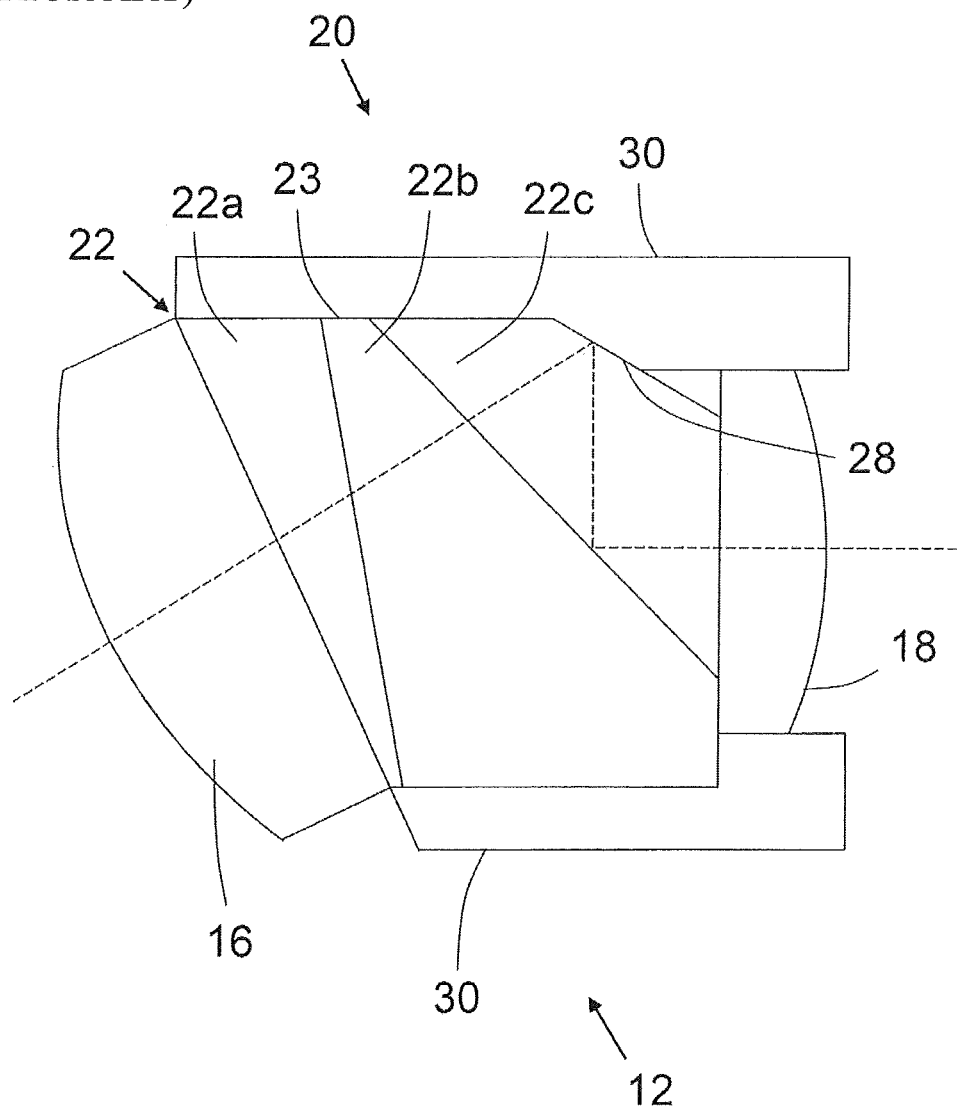
FIG. 2 illustrates a schematically simplified longitudinal section through a deflection prism assembly having an inlet lens and an outlet lens according to the prior art.

FIG. 2 schematically shows a deflection prism assembly 20 according to the prior art. The deflection prism assembly 20 comprises a deflection prism 22 which consists of three sub-prisms 22a, 22b, 22c, and a cylindrical prism holder 30. The prism holder 30 encloses a lateral surface 23 of the deflection prism 22 completely. Likewise, an inlet lens 16 and an outlet lens 18 are shown, which are not however part of the deflection prism assembly 20.

Incident light from an observation area, which is represented by a dashed line, enters the deflection prism 22 through the inlet window 10, which is not represented in FIG. 2, and the inlet lens 16. The light is reflected a first time by the reflection surface 28 before it is reflected a second time by the boundary between the second sub-prism 22b and the third sub-prism 22c substantially in a direction parallel to the endoscope axis. The light is conducted further via the outlet lens 18 in the direction of the interior of the endoscope.

Figure 3:
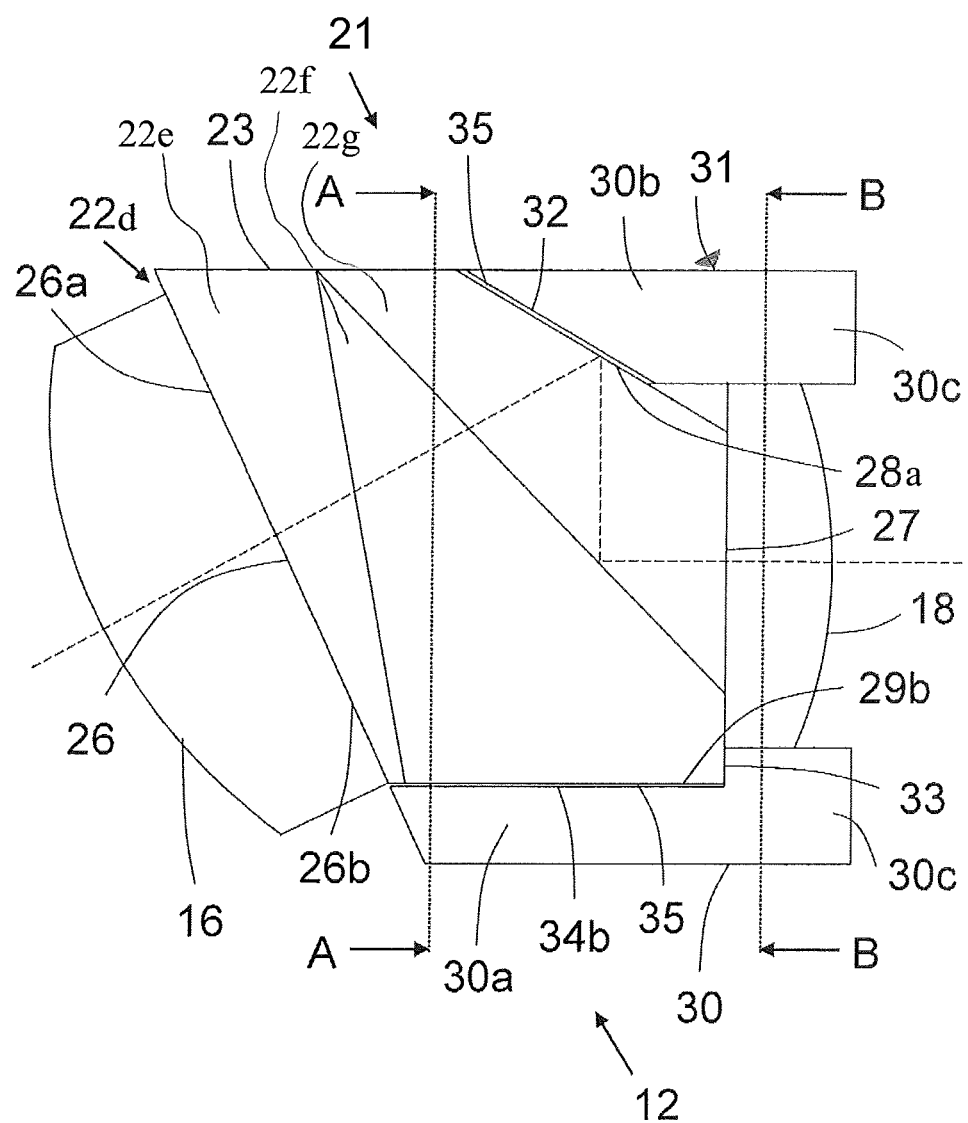
FIG. 3 illustrates a schematically simplified longitudinal section through a deflection prism assembly having an inlet lens and an outlet lens.

An exemplary beam path of a light beam is shown with the dashed line in FIG. 2 and FIG. 3 which, coming from the center of the field of view of the endoscope 2, substantially hits the inlet window 16.

A deflection prism assembly 21 according to an embodiment is schematically shown in FIG. 3. Compared with the cylindrical prism holder 30 according to the prior art in FIG. 2, the prism holder 31 according to the invention in FIG. 3 comprises a first part 30a, a second part 30b and an annular stop 30c.

The first part 30a has a substantially sledge-shaped form and extends from a near partial surface 26b of the light inlet surface 26 to a light outlet surface 27 of the deflection prism 22d. In the circumferential direction, the first part 30a encloses the outer circumference of the lateral surface 23 at an angle of approximately 150° (see FIG. 4a). A second part 30b extends from the reflection surface 28a in a proximal direction and has a substantially wedge-shaped form. In the region of the outlet lens 18, the first part 30a and the second part 30b are connected by the annular stop 30c (see FIG. 5).

The deflection prism assembly 21 is distinguished in that regions of the prism holder 31 are omitted, compared with a conventional prism holder, as it is shown by way of example in FIG. 2. In the omitted regions, the deflection prism 22d (including sub-prisms 22e, 22f and 22g) is enlarged accordingly. This concerns inter alia the regions which are located at the top in the diagram of FIG. 3 and which are adjacent to the distant partial surface 26a of the light inlet surface 26. Most notably, the reflection surface 28a is larger. By enlarging the deflection prism 22d, the optical properties of the endoscope 2 can be improved and the light intensity thereof increased.

At the same time, it is ensured with the deflection prism assembly 21 that, despite the omission on the prism holder 30, the deflection prism 22d is aligned precisely and is fixed stably in the prism holder 31.

For fixing purposes, the deflection prism 22b has bottom surfaces 29a, 29b, 29c on the lower side, of which only the bottom surface 29b is visible in the longitudinal section shown in FIG. 3. The bottom surfaces 29a, 29b, 29c are perpendicular to the light outlet surface 27 and are configured with a complementary shape to the lower holding surfaces 34a, 34b, 34c of the first part 30a of the prism holder 31. The bottom surfaces 29a, 29b, 29c and the lower holding surfaces 34a, 34b, 34c are separated by an adhesive gap 35. The adhesive gap 35 is necessary since the bottom surfaces 29a, 29b, 29c are only used for fixing, but not for aligning the deflection prism 22d.

The second part 30b of the prism holder 31 has an upper holding surface 32. This has a complementary shape to the reflection surface 28a and is fixed to the latter, for example with a suitable adhesive. Between the upper holding surface 32 and the reflection surface 28a there is located an adhesive gap 35.

In order to align the deflection prism 22d, a region of the light outlet surface 27 rests on a contact surface 33 of the stop 30c. In this way, a tilting of the deflection prism 32 is minimized or even excluded.

Figure 4A:
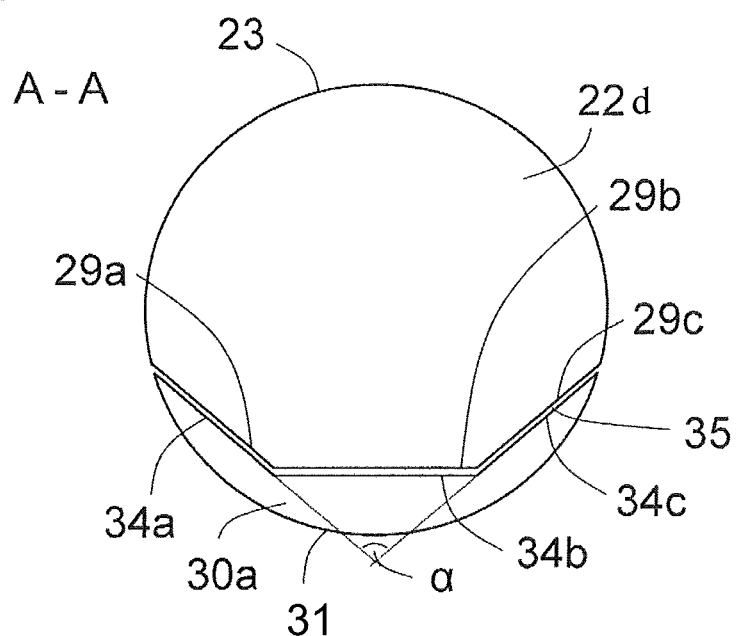
FIG. 4a illustrates a schematically simplified cross-section through a deflection prism assembly in the region of the light inlet surface.
Figure 4B:
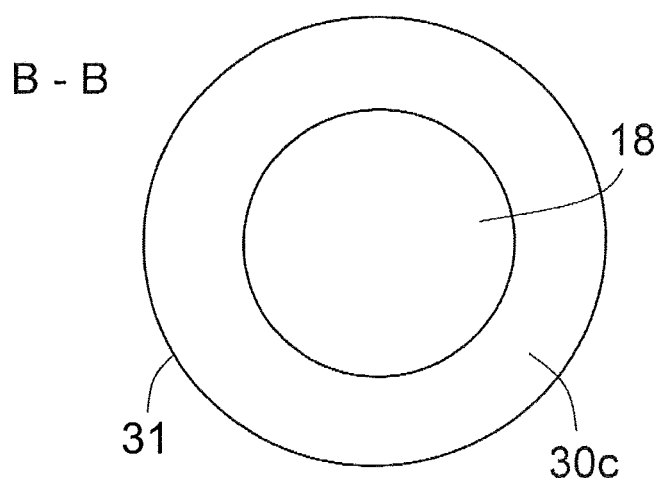
FIG. 4b illustrates a schematically simplified cross-section through a deflection prism assembly in the region of the light outlet lens.

FIGS. 4a and 4b schematically show cross-sections of the deflection prism assembly 21 along the lines A-A and B-B in FIG. 3. As FIG. 4a shows, the first part 30a of the prism holder 31 encloses the lateral surface 23 in an angle range of the outer circumference of approximately 150°.

In order to make it possible to center the deflection prism 22d exactly, the lateral surface 23 is circular in the part of the outer circumference, which is not enclosed. In the case of the example shown in FIG. 4a, this is approximately 210°.

On the underside, the deflection prism 22d has three bottom surfaces 29a, 29b, 29c which have a complementary shape to the lower holding surfaces 34a, 34b, 34c of the prism holder 31. Between the bottom surfaces 29a, 29b, 29c and the holding surfaces 34a, 34b, 34c there is located the adhesive gap 35 for this purpose.

In order to protect the deflection prism 22d from slipping under the action of shear forces, the bottom surfaces 29a, 29b, 29c can be arranged at a total angle α of approximately 90°. That is to say, the total of the angles of the adjacent lower holding surfaces 34a, 34b, 34c is approximately 90°. This embodiment is a compromise between the resistance to shear forces and the possibility of centering the deflection prism 22d.

A cross-section along the line B-B, which is shown in FIG. 4b, runs through a region of the deflection prism assembly 21, in which the stop 30c of the prism holder 31 encloses the outlet lens 18. In this cross-sectional plane, the prism holder 31 is round. In this way, both the stability of the prism holder 31 is guaranteed and a radial alignment, i.e. centering, is made possible. To this end, the circular outer circumference of the prism holder 31 is brought into alignment with the circular part of the outer circumference of the lateral surface 23 of the deflection prism 22d and this is, in turn, aligned with the endoscope axis. In this way, a precise alignment of the deflection prism 22d is possible, which avoids vignetting and image cutting.

Figure 5:
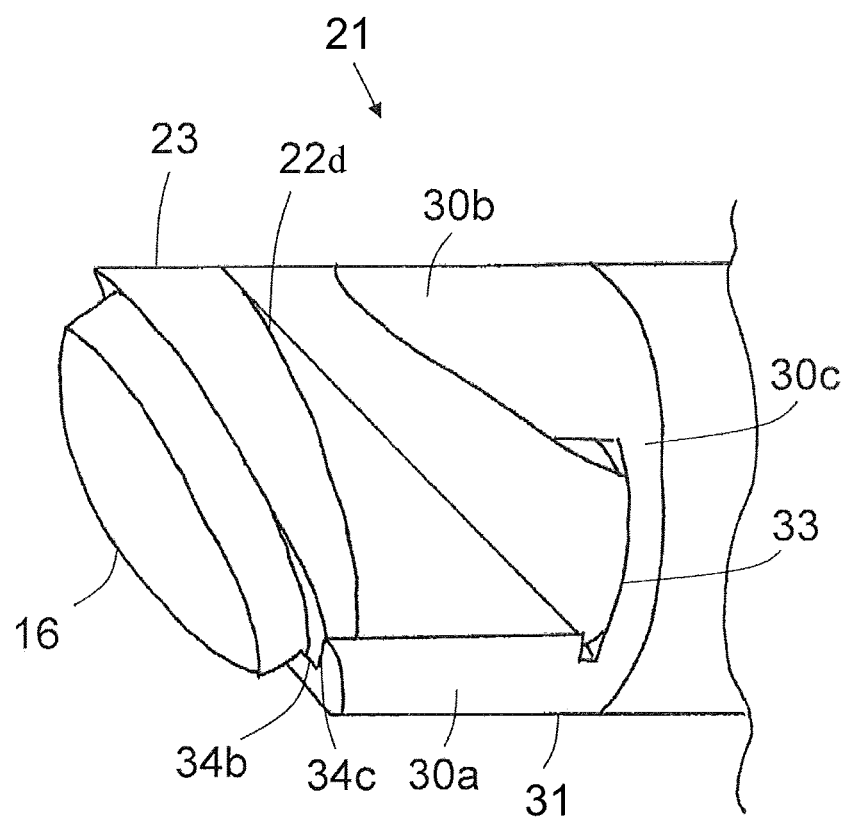
FIG. 5 illustrates a schematically simplified, perspective diagram of a deflection prism assembly.

FIG. 5 shows a schematically simplified perspective diagram of the deflection prism assembly 21, in which the form of the prism holder 31 is made obvious. The form and arrangement of the sledge-shaped first part 30a, the wedge-shaped second part 30b and the annular stop 30c can be seen. Furthermore, it can be seen that the prism holder 31 does not completely enclose the lateral surface 23 along any outer circumference of the lateral surface 23, that is to say the first part 30a does not join the second part 30b at any point. The connection between the first part 30a and the second part 30b exists solely in the stop 30c which, however, rests in a proximal direction on the deflection prism 22d and does not enclose this. Likewise, it can be seen that the deflection prism 22d rests with the light outlet surface 27 on the contact surface 33 of the annular stop 30c.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Endoscope
4 Handle
6 Shaft
8 Distal end
10 Inlet window
12 Distal end region
16 Inlet lens
18 Outlet lens
20 Deflection prism assembly
21 Deflection Prism Assembly
22 Deflection prism
22a-22c Sub-prism
22d Deflection Prism
22e-22g Sub-prism
23 Lateral surface
29 Light inlet surface
26a Distant partial surface
26b Near partial surface 27 Light outlet surface
28 Reflection surface
28a Reflection Surface
29a-29c Bottom surface
30 Prism holder
31 Prism Holder
30a First part
30b Second part
30c Stop
32 Upper holding surface
33 Contact surface
34a-34c Lower holding surface
35 Adhesive gap
α Angle

What is claimed is:

1. A deflection prism assembly for an endoscope having a lateral viewing direction, the deflection prism assembly comprising:
   a prism holder; and
   a deflection prism accommodated in the prism holder;
   wherein the deflection prism has a light outlet surface and an opposite light inlet surface arranged obliquely to the light outlet surface, the deflection prism further having a lateral surface extending between the light inlet surface and the light outlet surface;
   the prism holder accommodates the deflection prism such that the prism holder surrounds less than all regions of the lateral surface of the deflection prism; and
   the prism holder comprises a first part and a second part, the first part extending along an entire length of the deflection prism and the second part extending along a portion of the length less than the entire length, wherein the length is an extension of the deflection prism in a direction perpendicular to a light outlet plane, wherein the second part of the prism holder comprises a wedge shaped upper holding surface extending diagonal to the length of the deflection prism, wherein a reflection surface of the deflection prism extending diagonal to the length of the deflection prism is arranged parallel to the upper holding surface.

2. The deflection prism assembly according to claim 1, wherein the prism holder is formed such that the prism holder does not completely enclose the deflection prism at any outer circumferences of the deflection prism, wherein the outer circumferences extend parallel to the light outlet surface on the lateral surface of the deflection prism.

3. The deflection prism assembly according to claim 1, wherein, due to the oblique arrangement, the light inlet surface has a near partial surface and a distant partial surface with respect to the light outlet surface, wherein the first part of the prism holder extends from the light outlet surface to the near partial surface and the second part of the prism holder extends from the light outlet surface in a direction of the distant partial surface.

4. The deflection prism assembly according to claim 1, wherein the first part of the prism holder comprises a lower holding surface and the deflection prism comprises a bottom surface having a complementary shape, wherein the lower holding surface and the bottom surface are arranged perpendicularly to the light outlet surface and the bottom surface is fixed to the lower holding surface.

5. The deflection prism assembly according to claim 4, wherein the lower holding surface comprises at least two adjacent lower holding surfaces and the bottom surface comprises bottom surfaces associated with the at least two adjacent lower holding surfaces.

6. The deflection prism assembly according to claim 5, wherein a total angle is between 60° and 120°, the total angle being a total of the individual angles of the at least two adjacent lower holding surfaces.

7. The deflection prism assembly according to claim 6, wherein the total angle is 90°.

8. The deflection prism assembly according to claim 4, wherein the first part and the second part are connected by a stop of the prism holder.

9. The deflection prism assembly according to claim 8, wherein the stop is annular.

10. The deflection prism assembly according to claim 8, wherein the stop comprises a contact surface which is plane parallel to the light outlet surface of the deflection prism, wherein the light outlet surface rests on a region of the contact surface.

11. The deflection prism assembly according to claim 10, wherein a gap width is provided between one or more of the lower holding surface and the associated bottom surface or between the upper holding surface and the associated reflection surface, wherein the gap width is such that the lower holding surface does not rest on any point of the bottom surface and/or the upper holding surface does not rest on any point of the reflection surface, when the light outlet surface rests on the region of the contact surface.

12. The deflection prism assembly according to a claim 1, wherein at least one third of an outer circumference of the lateral surface is circular.

13. The deflection prism assembly according to a claim 12, wherein at least two thirds of the outer circumference of the lateral surface is circular.

14. The deflection prism assembly according to claim 1, wherein at least one third of an outer circumference of the prism holder is circular.

15. The deflection prism assembly according to claim 1, wherein a complete outer circumference of the prism holder is circular.

16. An endoscope, comprising:
   a shaft; and
   the deflection prism assembly according to claim 1 disposed in the shaft.

* * * * *